(12) United States Patent
Karlsson et al.

(10) Patent No.: US 9,033,934 B2
(45) Date of Patent: May 19, 2015

(54) MEDICAL DELIVERY DEVICE WITH AN INITIAL LOCKED STATE, INTERMEDIATE PRIMING STATE AND A MEDICAMENT DELIVERY STATE

(75) Inventors: Sebastian Karlsson, Sundbyberg (SE); Mattias Daniel, Stockholm (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 14/347,484

(22) PCT Filed: Sep. 12, 2012

(86) PCT No.: PCT/SE2012/050961
§ 371 (c)(1),
(2), (4) Date: Mar. 26, 2014

(87) PCT Pub. No.: WO2013/048310
PCT Pub. Date: Apr. 4, 2013

(65) Prior Publication Data
US 2014/0228769 A1    Aug. 14, 2014

Related U.S. Application Data

(60) Provisional application No. 61/539,650, filed on Sep. 27, 2011.

(30) Foreign Application Priority Data

Sep. 27, 2011 (SE) ...................................... 1150883

(51) Int. Cl.
*A61M 5/32* (2006.01)
*A61M 5/315* (2006.01)
*A61M 5/20* (2006.01)

(52) U.S. Cl.
CPC ......... *A61M 5/31505* (2013.01); *A61M 5/2033* (2013.01); *A61M 5/31548* (2013.01); *A61M 5/3213* (2013.01); *A61M 5/20* (2013.01); *A61M 5/31553* (2013.01)

(58) Field of Classification Search
CPC . A61M 5/2033; A61M 5/20; A61M 5/31505; A61M 5/31548; A61M 5/31553; A61M 5/3213; A61M 2005/2013; A61M 2005/2073; A61M 5/3146; A61M 5/24; A61M 5/31525; A61M 5/31583; A61M 5/3257
USPC ........................................................ 604/197
See application file for complete search history.

(56) References Cited

U.S. PATENT DOCUMENTS 6,893,420 B2    5/2005 Arnisolle
7,112,187 B2 *  9/2006 Karlsson ...................... 604/187
(Continued)

FOREIGN PATENT DOCUMENTS

EP           1932558 A1    6/2008
WO     2004/028598 A1    4/2004
(Continued)

OTHER PUBLICATIONS

Sweden Patent Office, Int'l Search Report in PCT/SE2012/050961, Jan. 9, 2013.
Sweden Patent Office, Written Opinion in PCT/SE2012/050961, Jan. 9, 2013.

*Primary Examiner* — Jason Flick
(74) *Attorney, Agent, or Firm* — Piedmont Intellectual Property

(57) ABSTRACT

Provided is a medicament delivery device having an initial locked state, an intermediate priming state, and a medicament delivery state. The medicament delivery device is configured such that individual dose setting and activation of medicament delivery is prevented until the cap at the proximate end of the medicament delivery device is removed.

23 Claims, 15 Drawing Sheets

(56) References Cited

U.S. PATENT DOCUMENTS 7,597,685 B2 * 10/2009 Olson .......................... 604/208
2006/0270984 A1    11/2006 Hommann
2006/0270985 A1 * 11/2006 Hommann et al. ........... 604/136

FOREIGN PATENT DOCUMENTS

| WO | 2006/057604 A1 | 6/2006 |
| WO | 2010/033882 A2 | 3/2010 |

* cited by examiner

MEDICAL DELIVERY DEVICE WITH AN INITIAL LOCKED STATE, INTERMEDIATE PRIMING STATE AND A MEDICAMENT DELIVERY STATE

TECHNICAL FIELD

Provided is a medicament delivery device having an initial locked state, an intermediate priming state, and a medicament delivery state. The medicament delivery device is configured such that individual dose setting and activation of medicament delivery is prevented until the cap at the proximate end of the medicament delivery device is removed.

BACKGROUND

One solution for keeping a medicament delivery device as pre-assembled as possible is to deliver the medicament delivery device with a delivery member, such as a needle, pre-attached. This solution often causes the rear end of the needle to protrude into the interior of the container, which could be a drawback if the medicament reacts with the material of the delivery member when exposed for a period of time. In that respect it would be desirable to have the rear part of the delivery member outside the container until the delivery is to be performed. To minimize the number of actions needed in order to perform an injection, some devices only need to be pressed against the injection area, without the need of injecting by pressing a button or the like, which causes the needle to penetrate the injection area and the device perform the injection. Thereby, the delivery procedure is reduced by at least one step.

A disadvantage of prior art solutions is that they sometimes are unreliable and may unintentionally be actuated. U.S. Pat. No. 6,893,420 discloses a device arranged with a locking means for locking a ledge that prevents the automatic penetration and injection means from being released before mixing of the medicament is finished. However, this device suffers from the disadvantage of a user having to remove the locking means actively from the device after the mixing is finished, thereby causing an unnecessary step which may be disadvantageous, and especially considering emergency usage of such device.

It is therefore an objection of the invention to provide a medicament delivery device that is both reliable and safe to use and that is easy to use when handling.

SUMMARY OF THE INVENTION

In order to overcome one or several of the above-mentioned problems, a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The invention provides a medicament delivery device. The medicament delivery device has an initial locked state, an intermediate priming state, and a medicament delivery state.

According to an embodiment, the medicament delivery device comprises a housing having a proximal end and a distal end. A medicament container holder is arranged within the housing. A plunger rod is also arranged within the housing.

The housing of the medicament delivery device may comprises a window that allows the user to view the progress of medicament delivery, i.e. whether the medicament delivery device is still in its initial stage with the medicament not yet being injected, or whether the medicament container is already emptied. A user can see the medicament container accommodated in the housing.

Preferably, at the proximal end of the housing, a further window is provided that is used to indicate a set dose to a user.

The plunger rod, a resilient member, and a plunger rod guide rod may form a plunger assembly. These three elements are preferably coaxially arranged in that the plunger resilient member is at least with its proximal part received in a central bore of the plunger rod. Furthermore, the plunger rod guide rod may extend at least into the distal part of the plunger resilient member.

The plunger rod comprises a plunger rod proximal end and a plunger rod distal end. At least one plunger rod stop rib is arranged at the outer surface of the plunger rod at its distal part. For example, two such ribs are provided spaced at 180° to each other. These plunger rod stop ribs extend axially, i.e. in longitudinal direction of the medicament delivery device. Such plunger rod stop rib is slidably receivable in corresponding grooves at the inner surface of the medicament container holder.

The medicament delivery device further comprises a plunger locking means that is rotatable in relation to the housing and to the plunger rod. The plunger locking means is configured to hold the plunger rod in its initial locked position in the initial locked state of the medicament delivery device. The plunger locking means is also configured to release the plunger rod from its initial locked position towards the proximal end of the medicament delivery device to an intermediate priming position. Furthermore, the plunger locking means is configured to hold the plunger rod in the intermediate priming position, and to release the plunger rod from its intermediate priming position towards the proximal end of the medicament delivery device to a final delivery position.

The plunger locking means may comprise an inner an abutment surface that is formed by an inner step of the plunger locking means. Such abutment surface provides a reduced diameter of the plunger locking means at its distal end compared to the proximal part of the plunger locking means. This abutment surface forms a distal support surface against the distal end of the housing of the medicament container holder.

Furthermore, the plunger locking means may have two plunger rod abutment surfaces spaced axially and circumferentially from each other. The plunger rod abutment surfaces project from the inner surface of the plunger locking means. Both abutment surfaces face distally, i.e. form abutments against proximal movements of the plunger rod. The more distal abutment surface forms an initial abutment surface for the plunger rod. In particular, a plunger rod stop rib provided at the outer surface of the plunger rod abuts axially against the initial abutment surface when the medicament delivery device is in its initial locked state. In the intermediate priming state, the plunger rod stop rib is rotationally and axially moved and then abuts against the second abutment surface, which forms a priming abutment surface.

Thus, in the initial state of the medicament delivery device, the plunger rod stop rib abuts against the initial abutment surface. In the priming state of the medicament delivery device, the plunger rod stop rib abuts against the priming abutment surface. Thus, the plunger locking means has been rotated relative to the plunger rod, and due to the force applied onto the plunger rod by the plunger resilient member, the plunger rod was moved axially towards the proximal end of the medicament delivery device, and then abuts against the priming abutment surface.

The medicament container holder may be configured for accommodating a medicament container. The medicament container may have a stopper sealingly and slidable arranged inside the medicament container. The plunger rod may be arranged with the proximal end thereof contactable with the stopper.

The medicament container holder may comprise in its distal part one or more inner dose grooves having different axial lengths. When a dose is set by a user, the plunger locking means is rotated relative to the medicament container holder and is brought into alignment with an appropriate inner dose groove in the medicament container holder.

A shield sleeve is arranged slidable at least in a proximal part of the housing, and a further resilient member or energy accumulating member is associated with the shield sleeve. The shied sleeve may comprises a window that is aligned with viewing window of housing.

At its proximal end, the medicament delivery device comprises a cap assembly which is associated to or connected to the medicament container holder. The cap assembly comprises removable outer cap. The outer cap is removed before use of the medicament delivery device as described in more detail below.

The medicament delivery device further comprises a dose setting mechanism that is locked in the initial locked state of the medicament delivery device so that unintentional dose setting prior to use of the medicament delivery device is prevented.

In the initial locked position of the medicament delivery device, the shield sleeve is locked by the outer cap from being axially moveable towards the proximal end of the medicament delivery device to a second position. The shield sleeve, when being moved in its second position by the plunger resilient member upon removal of the outer cap is locked in the second position by the plunger locking means. Furthermore, movement of the shield sleeve to its second position results in release of the dose setting mechanism so that at this stage a dose can be set. A dose setting by the dose setting mechanism releases the locking of the shield sleeve in its second position, thus allowing a medicament delivery to be performed.

Movement of the shield sleeve to its second position may result in rotation of the plunger locking means to release the plunger rod from its initial locked position to its intermediate priming position.

It is preferred that the shield sleeve and the plunger locking means are operationally connected such that axial movement of the shield sleeve towards the distal end of the medicament delivery device, when the shield sleeve is pressed against a delivery site, causes the plunger locking means to perform a rotational movement. The rotational movement of the plunger locking means may result in a release of the plunger rod from its priming position. Furthermore, upon release of the plunger rod, the plunger rod is urged towards the proximal end of the medicament delivery device whereby a medicament delivery is performed.

The plunger resilient means may be configured to urge further the shield sleeve towards the proximal end of the medicament delivery device when the shield sleeve is removed from the delivery site. The medicament delivery device may further comprise a locking means for locking the shield sleeve against moving towards the distal end of the medicament delivery device when the shield sleeve is removed from the delivery site. The shield sleeve locking means may be formed by the plunger locking means.

The operational connection between the shield sleeve and the plunger locking means may be formed by a cam-groove-mechanism.

The medicament delivery device may further comprise a shield driver being operationally associated with the shield resilient member such that due to an output axial force from the plunger resilient member, the shield sleeve is axially moveable in relation to the housing a predetermined distance towards the proximal end of the medicament delivery device from its initial locked position to its second position whereby the medicament delivery device is brought to its priming state.

The shield driver may have a distal part and a shield driver flange at its proximal end. The shield driver flange serves as a proximal abutment surface for the plunger resilient member that is at least with its proximal part coaxially arranged around the outer surface of shield driver. In the loaded state of the medicament delivery device, the plunger resilient member is fully surrounding the shield driver. The plunger resilient member is used to axially move the shield driver in order to perform a priming of the medicament delivery device and to subsequently initiate delivery of the medicament.

The medicament container holder is preferably coaxially arranged within the shield sleeve. In the fully assembled state of the medicament delivery device, the medicament container holder is at least with its proximal part located within the shield sleeve. The distal part of the medicament container holder may be arranged coaxially within the plunger locking means. The medicament container holder comprises one or more housing connection features, such as radial protrusions that allow connecting the medicament container holder to the housing.

In a preferred embodiment, the cap assembly further comprises a retainer member connectable to the medicament container holder. The cap assembly may further comprise a hub coaxially movable within the retainer member. The hub may comprise a needle having a proximal end and a distal end. The cap assembly may further comprise an inner cap interactively connected to the hub and the retainer member. The outer cap may coaxially be arranged to the inner cap. The engagement between the outer cap and the inner cap and between the inner cap and the retainer member may be configured such that removal of the outer cap causes the hub to move distally such that the distal end of the needle penetrates the proximal end of the medicament container.

The cap assembly may further comprise an outer cap clutch provided between the outer cap and a shield front. In the fully assembled state of the medicament delivery device, the outer cap clutch prevents the user from applying an excessive force in the wrong direction when removing the outer cap from the cap assembly. Thus, cap clutch ensures that the outer cap is correctly removed in the right rotational direction.

The shield front may comprise one or more shield front engagement structures. With such engagement structures, the shield front is connectable with the proximal part of the shield sleeve. That is, in the assembled state, the shield front forms the most proximal end of the shield sleeve.

The cap assembly comprises a cap sub-assembly 90' that is formed by the retainer member. The retainer member may also comprise an outer thread structure onto which an inner cap can be screwed. Within the inner cap, the hub is located having an engagement part. The engagement part of the hub is with its distal part preferably engaged to a corresponding engagement structure of the retainer member.

The cap assembly is configured such that when the user starts to turn (e.g., in counter-clockwise direction) the outer cap in order to remove it from the fully assembled medicament delivery device, due to a respective engagement of the outer cap with the inner cap, turning of the outer cap to remove it proximally causes the hub to be screwed distally into the retainer member whereby the pointed distal end of the needle penetrates the sterile barrier and subsequently the membrane of the medicament container. Finally, the outer cap and the inner cap can be removed. Preferably, the pitches of the threads are chosen such that there is a major longitudinal movement of the hub in the distal direction for a small turning angle in order to prevent as much as possible turning or "drilling" of the distal end of the needle in the membrane of the medicament container. At the same time, the pitch of the threads between the outer cap and the retainer member is preferably chosen such that the user only needs to turn the outer cap preferably about half a turn in order to perform the removal operation so as to avoid having to change grip in order to finish the operation.

In the initial state, the shield driver may engage with an inner guide protrusion into the outer groove structure of the cam-groove structure of the plunger locking means. That is, the shield driver is connected to the plunger locking means by guiding means on tracks of the plunger locking means.

The shield driver flange may comprise a plurality of shield driver flange indentations which receive axial ribs provided on the inner surface of the housing that provide a shield link rotational lock structure. Due to this lock structure, in the initial state of the medicament delivery device, the shield driver is rotatably locked to the housing but axially slidable in relation to the housing. The housing may comprise at its inner surface shield link rotational lock structure, for example in the form of one or more axial ribs.

In a preferred embodiment of the medicament delivery device the dose setting mechanism comprises a dose member having a dose knob projecting distally from the housing and a dose member engagement part proximal to the dose knob. Furthermore, the dose setting mechanism comprises a tubular increment element being coaxial to the dose member engagement part. It is preferred that the dose member engagement is arranged coaxially within the dose setting mechanism.

The dose member engagement part may comprise an outer rotational lock structure for rotationally locking the dose member to a mating inner lock structure of the tubular increment element. The tubular increment element may comprise an outer lock structure for rotationally locking the tubular increment element to a mating inner lock structure of the shield link.

Thus, the dose member may comprise a proximal dose member engagement part having an outer rotational lock structure, and with a dose knob at its distal end. The dose knob may be is gripped by a user for setting a dose by rotating the dose knob. Such rotation is transferred via the proximal dose member engagement part to other components of the medicament delivery device. The rotational lock structure may interact with a corresponding lock structure at the inner surface of the tubular increment element.

The tubular increment element may comprise an outer circumferential ledge forming a distal abutment surface for the shield resilient member. It is also encompassed by the invention that the first resilient member may be in contact with a ledge provided at the inside of the distal housing part, proximal to the ledge of the tubular increment element.

The tubular increment element may also comprises at its outer surface a shield link lock structure that engages with a corresponding lock structure at the inner surface of the shield driver.

The tubular increment element may also comprise a distal cam feature mating with a distal cam feature of the housing. The mating cam features are configured to allow distal movement of the tubular increment element during rotational movement of the tubular increment element.

BRIEF DESCRIPTION OF THE DRAWINGS

The following Figures below disclose an embodiment of the invention for illustrational purposes only. In particular, the disclosure within the Figures is not meant to limit the range of protection of the invention. The embodiment shown may be modified in many ways within the scope of the claims.

DETAILED DESCRIPTION OF THE DRAWINGS

Figure 1:
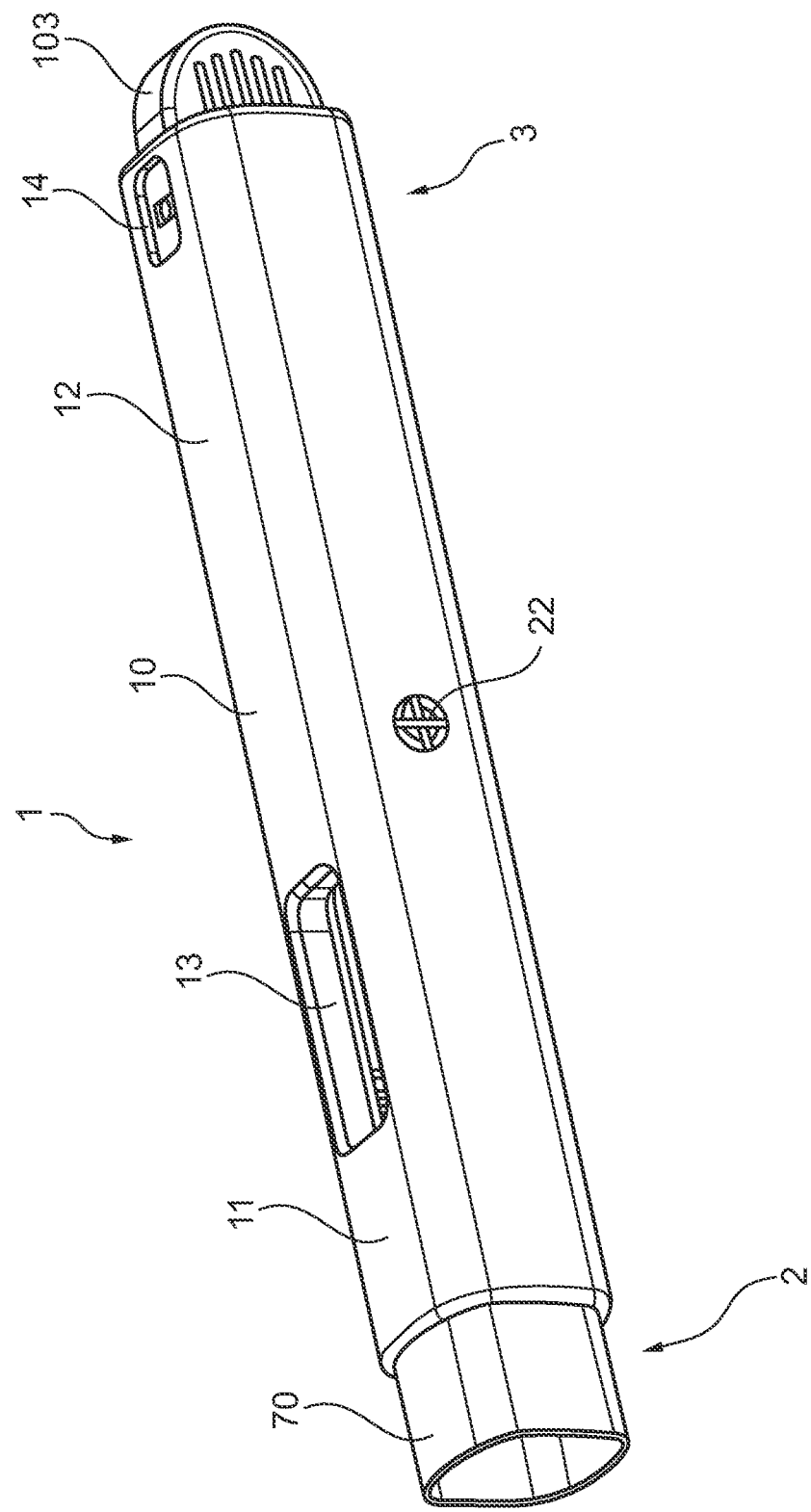
FIG. 1 shows a perspective view of a medicament delivery device according to a preferred embodiment of the invention.

FIG. 1 shows a perspective view of a medicament delivery device 1 according to a preferred embodiment of the invention. The medicament delivery device 1 has a proximal end 2 and a distal end 3 and comprises a housing 10 having a proximal part or end 11 and a distal part or end 12. In the assembled state of the medicament delivery device 1, the housing 10 forms the outer surface or appearance of the medicament delivery device 1. In the perspective view of FIG. 1, the medicament delivery device 1 is not yet fully assembled, and a shield sleeve 70 projects from the proximal end of the housing 10. Full assembly of the medicament delivery device 1 is described in more detail below, for example with reference to FIG. 3.

The housing 10 of the medicament delivery device 1 comprises a window 13 that allows the user to view the progress of medicament delivery, i.e. whether the medicament delivery device 1 is still in its initial stage with the medicament not yet being injected, or whether the medicament container is already emptied. Through window 13, the user can see the medicament container accommodated at least in the proximal part of the housing 10. In a preferred embodiment, two such windows are provided located at opposite sides of the housing 10.

Furthermore, at the proximal end 12 of the housing 10, a further window 14 is provided that is used to indicate a set dose to a user, as described in more detail below. At the proximal end 12 of housing 10, a dose knob 103 for dose setting projects distally.

Figure 2:
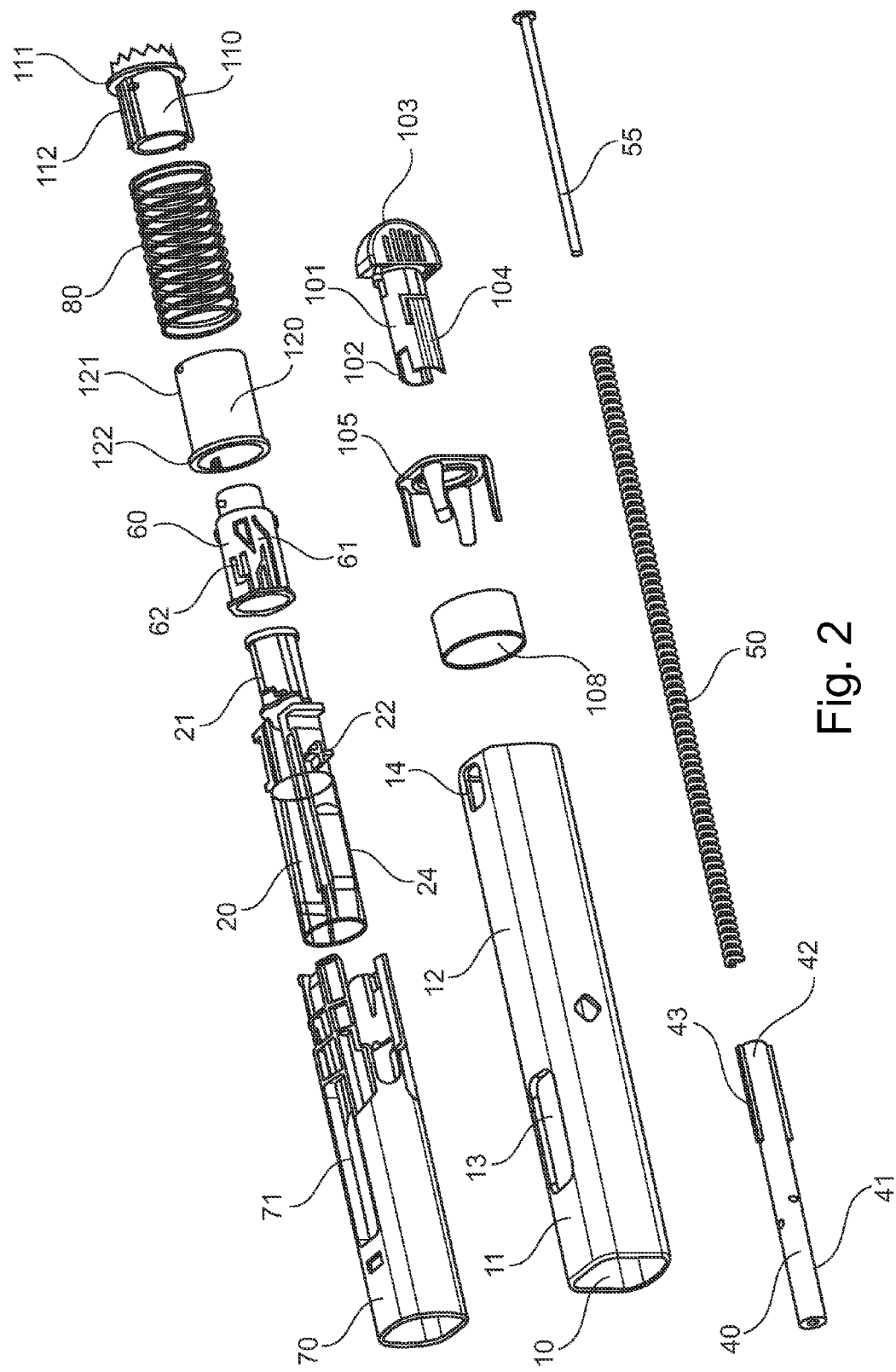
FIG. 2 shows an exploded view of the medicament delivery device according to the preferred embodiment of FIG. 1.

FIG. 2 shows an exploded view of the medicament delivery device 1 of the preferred embodiment shown in FIG. 1. Coaxially arranged within housing 10 is a shield sleeve 70 which also comprises a window 71 that is aligned with window 13 of housing 10. The medicament delivery device 1 further comprises a medicament container holder 20 that is coaxially arranged within shield sleeve 70. In the fully assembled state of the medicament delivery device 1, the medicament container holder 20 is at least with its proximal part located within the shield sleeve 70. The distal part 21 of the medicament container holder 20 is arranged coaxially within plunger locking means 60. The medicament container holder comprises one (or two opposing) housing connection features, such as radial protrusions, that allow connecting the medicament container holder 20 to the housing 10 (see also FIG. 1).

In the preferred embodiment shown in FIG. 2, the medicament container holder 20 comprises axial guide ribs 24. Preferably, the axial guide ribs are arranged at opposite sides of the medicament container holder 20, and extend in longitudinal direction thereof. The guide ribs 24 are received in corresponding groove structures provided at the inner surface of the proximal part of the shield sleeve 70 so that the shield sleeve 70 is axially movable in relation to the medicament container holder 20, and is also locked from being rotated relative to the housing 10 (in case of a cylindrical configuration).

Plunger locking means 60 is of generally cylindrical configuration and comprises an outer groove structure 61 and a shield link lock structure 62. These elements will be described in more detail below.

FIG. 2 further shows a shield driver 120 having a distal part 121 and a shield driver flange 122 at its proximal end. Shield driver flange 122 serves as a proximal abutment surface for the first resilient member or energy accumulating member 80 that is at least with its proximal part coaxially arranged around the outer surface of shield driver 120. In the loaded state of the medicament delivery device, the first resilient member 80 is fully surrounding the shield driver 120. The first resilient member, for example a spring, is used to axially move the shield driver 120 in order to perform a priming of the medicament delivery device 1 and to initiate delivery of the medicament. This will be described in more detail below.

FIG. 2 also shows a plunger assembly comprising a plunger rod 40, a second resilient member 50 (such as a spring), and a plunger rod guide rod 55. These three elements are coaxially arranged in that the second resilient member 50 is at least with its proximal part received in a central bore of the plunger rod 40. Furthermore, the plunger rod guide rod 55 extends into the distal part of the second resilient member 50.

The plunger rod comprises the plunger rod proximal end 41 and a plunger rod distal end 42. At least one plunger rod stop rib 43 is arranged at the outer surface of the plunger rod 40 at its distal part 42. For example, two such ribs are provided spaced at 180° to each other. These plunger rod stop ribs 43 extend axially, i.e. in longitudinal direction of the medicament delivery device. The plunger rod stop rib(s) 43 is slidably receivable in corresponding grooves at the inner surface of the medicament container holder 20, as will be described below.

FIG. 2 also shows the elements of a dose setting mechanism 100. The dose setting mechanism 100 comprises a dose member 101, a tubular increment element 110, an engagement element 105, and a dose drum 108.

The dose member 101 comprises a proximal dose member engagement part 102 with outer rotational lock structure 104, and dose knob 103 at its distal end. Dose knob 103 is gripped by a user for setting a dose by rotating the dose knob 103. Such rotation is transferred via the proximal dose member engagement part 102 to other components of the medicament delivery device 1, as described in more detail below. The rotational lock structure 104 interacts with a corresponding lock structure at the inner surface of the tubular increment element 110. The tubular increment element 110, in turn, comprises at its outer surface a shield link lock structure 112 that engages with a corresponding lock structure at the inner surface of the shield driver 120.

The tubular increment element 110 further comprises a circumferential ledge 111 which serves as a distal abutment surface for the first resilient member 80. Alternatively, the first resilient member 80 may be in contact with a ledge provided at the inside of the distal housing part, proximal to the ledge of the tubular increment element 110.

As can be seen in FIG. 2, all components of the medicament delivery device of this preferred embodiment are substantially tubular or cylindrical.

Figure 3:
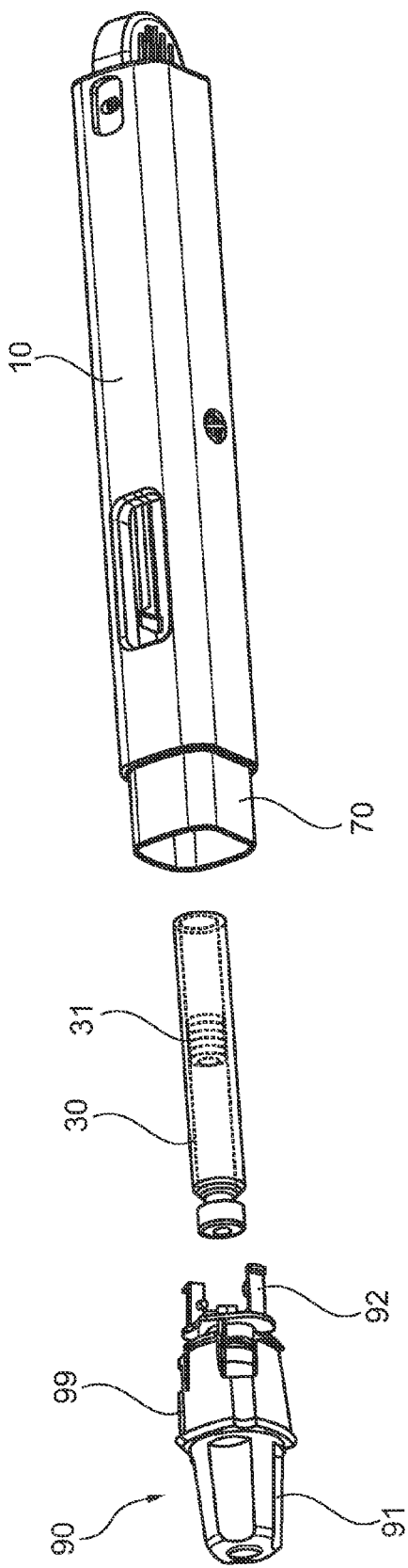
FIG. 3 shows a partly exploded view of the medicament delivery device according to the preferred embodiment of the invention.

FIG. 3 shows a partly exploded view of a medicament delivery device prior to full assembly according to the preferred embodiment of the invention. In addition to the elements already shown in FIG. 1, FIG. 3 shows the medicament container 30 with its internal stopper 31. FIG. 3 also shows a cap assembly 90 that comprises, among other elements, an outer cap 91, a retainer member 92, and a shield front 99. Further components of the cap assembly are described below in the context of FIGS. 4 and 5.

The cap assembly 90 and the medicament container 30 are inserted into the remaining already pre-assembled parts of the medicament delivery device 1 from its proximal end, as indicated by the two arrows shown in FIG. 3. Thus, a fully assembled medicament delivery device 1 is obtained.

Figure 4:
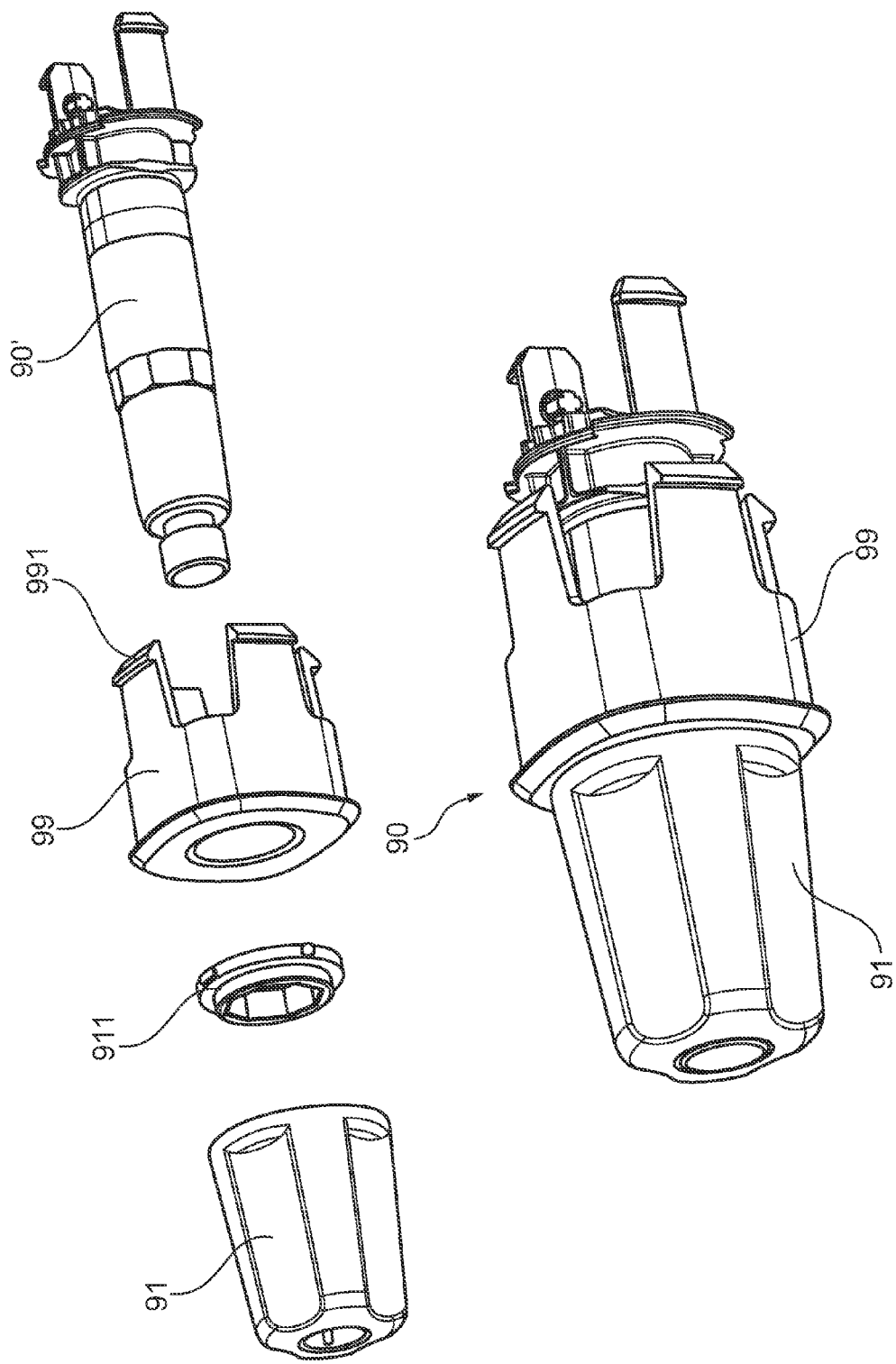
FIG. 4 shows an exploded view of the cap assembly of the medicament delivery device according to the preferred embodiment of the invention.

FIG. 4 shows the cap assembly of the medicament delivery device in its fully assembled state as well as in a partly disassembled state. As can be seen in FIG. 4, an outer cap clutch 911 is provided between the outer cap 91 and the shield front 99. In the fully assembled state of the medicament delivery device 1, the outer cap clutch 911 prevents the user from applying an excessive force in the wrong direction when removing the outer cap 91 from the cap assembly. Thus, cap clutch 911 ensures that the outer cap is correctly removed in the right rotational direction.

The shield front 99 comprises one or more shield front engagement structures 991 (in FIG. 4, four such engagement structures can be seen spaced at an angle of 90° to each other) with which the shield front 99 is connected with the proximal part of the shield sleeve 70. That is, in the assembled state, the shield front forms the most proximal end of the shield sleeve 70.

FIG. 4 furthermore shows cap sub-assembly 90'. Cap sub-assembly 90' is shown in a fully exploded view in FIG. 5. The sub-assembly 90' comprises a retainer member 92 having a distal locking structure 922 that project from the main body of the retainer member in distal direction. In the embodiment shown in FIG. 5, the retainer member 92 comprises two opposite locking structures 922. With these locking structures 922, the retainer member 92 is, in the assembled state, fixedly connected to the shield sleeve 70. The locking structure is formed by hook-like elements projecting radially at the distal ends of the locking structures. At the radially inner side of the locking structures 922, projections 922a are provided. With these projections, the retainer member 92 is locked to the medicament container holder 20.

The retainer member 92 also comprises an outer thread structure 923 onto which an inner cap 97 can be screwed. Within the inner cap 97, a hub 93 is located having an engagement part 931. The hub 93 further comprises a needle 94 having a proximal end 95 and a distal end 96.

The distal end 96 is configured to penetrate a membrane arranged at the proximal end of the medicament container 30. The hub 93 thus serves as a needle holder and is fixedly connected to the injection needle 94.

Figure 5:
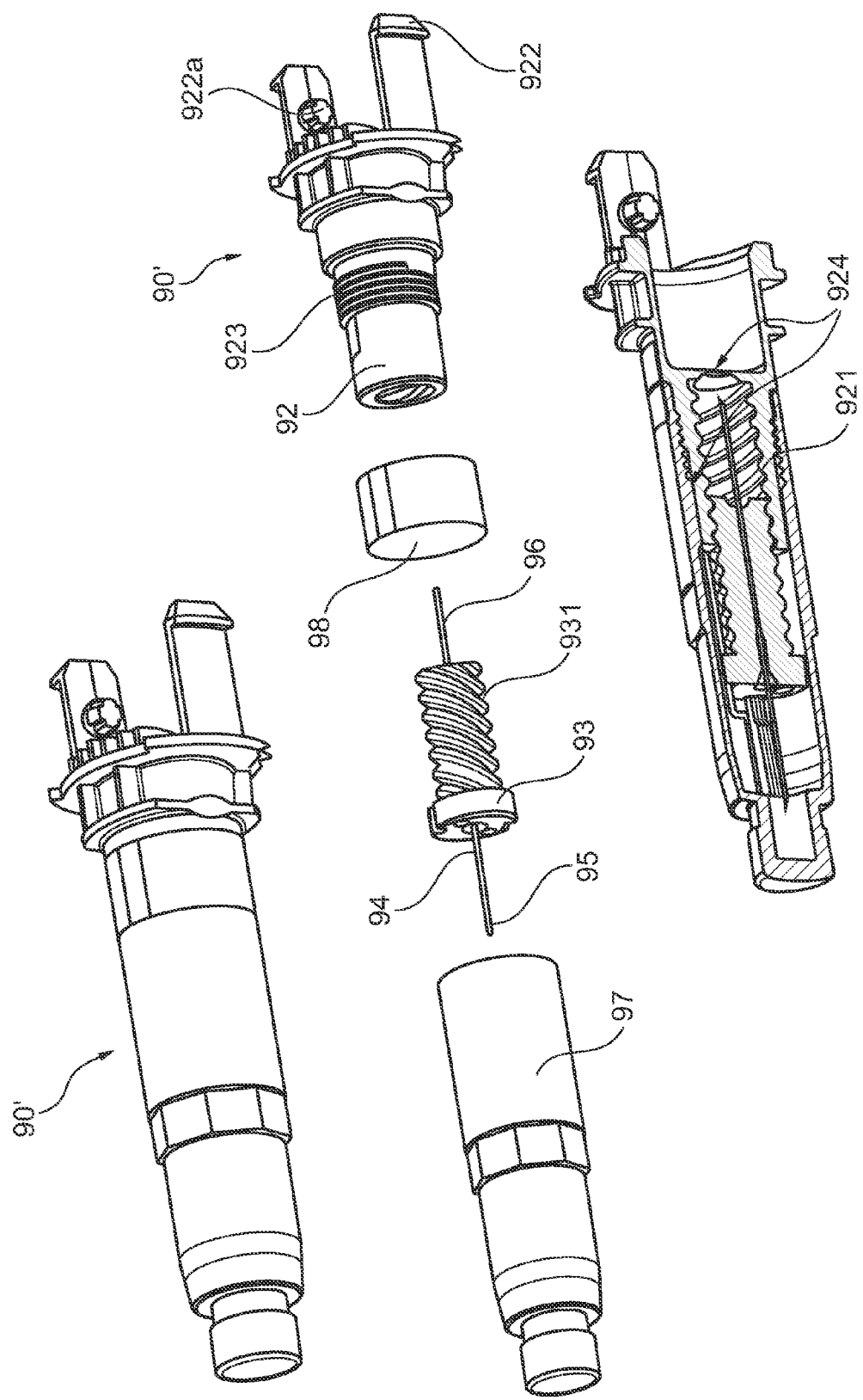
FIG. 5 shows an exploded view of parts of the cap assembly of the medicament delivery device according to the preferred embodiment of the invention.

As can be seen in the cross-sectional view of the sub-assembly 90', shown in FIG. 5, the engagement 931 of the hub 93 is with its distal part engaged to a corresponding engagement structure 921 of the retainer member 92. Two sterile barriers 924 are provided in order to keep the needle 94 in a sterile condition. As can be seen in FIG. 5, the distal tip of the needle 94 is spaced proximally from barrier 924.

Thus, in the initial stage of the medicament delivery device 1, the distal tip of the needle 94 is sufficiently spaced from the medicament container 30, which in the fully assembled state is located distally from sterile barrier 924. However, the mating engagement structures 921 and 931 are such that the needle can be displaced distally by a distal movement of the hub 93, for example by rotation.

The cap assembly 90 is configured such that when the user starts to turn (e.g., in counter-clockwise direction) the outer cap 91 in order to remove it from the fully assembled medicament delivery device, due to a respective engagement of the outer cap 91 with the inner cap 97, turning of the outer cap 91 to remove it proximally causes the hub 93 to be screwed distally into the retainer member 92 whereby the pointed distal end 96 of the needle 94 penetrates the sterile barrier 924 and subsequently the membrane of the medicament container 30. Finally, the outer cap 91 and the inner cap 97 can be removed. Preferably, the pitches of the threads are chosen such that there is a major longitudinal movement of the hub 93 in the distal direction for a small turning angle in order to prevent as much as possible turning or "drilling" of the distal end 96 of the needle 94 in the membrane of the medicament container 30. At the same time, the pitch of the threads between the outer cap 91 and the retainer member 92 is preferably chosen such that the user only needs to turn the outer cap 91 about half a turn in order to perform the removal operation so as to avoid having to change grip in order to finish the operation.

Figure 6:
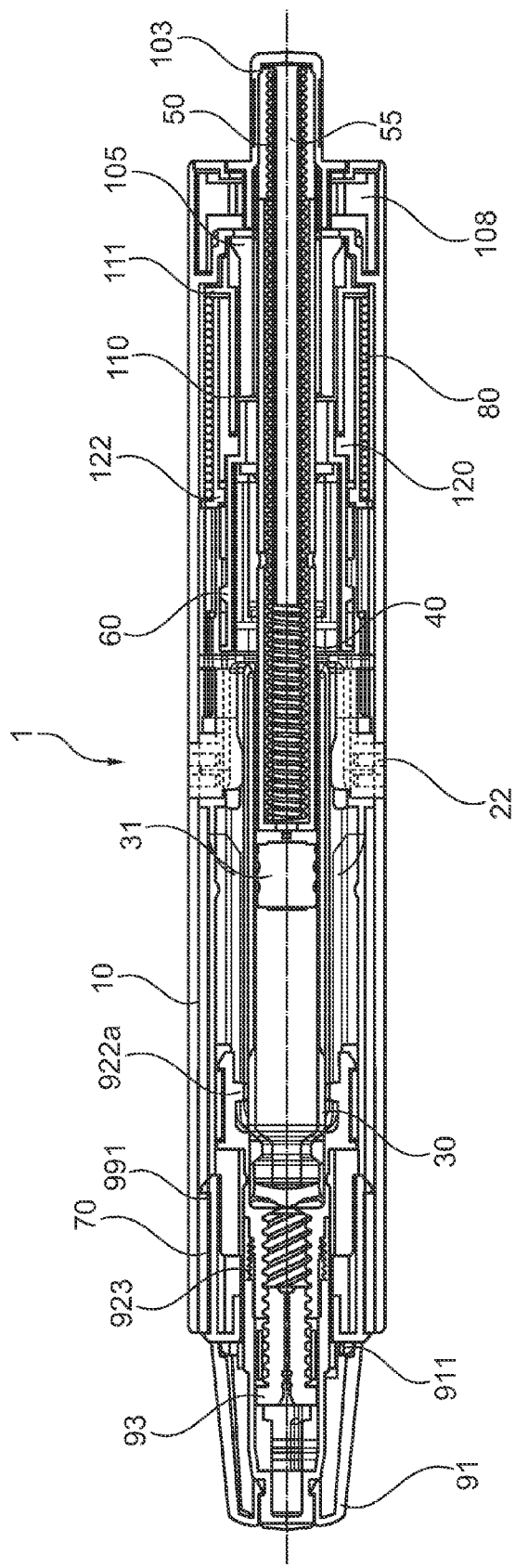
FIG. 6 shows a cross-sectional view of the medicament delivery device according to the preferred embodiment.

FIG. 6 shows a cross-sectional view of the medicament delivery device 1 in its fully assembled state. As can be seen in the left part of the drawing, the hub 93 is still located such that the distal end of the needle 94 is spaced from the membrane of the medicament container 30. FIG. 6 also shows the outer cap clutch 911 that prevents turning the outer cap 91 in the wrong direction. FIG. 6 also shows the outer thread 923 on the retainer 92 onto which the inner cap 97 is screwed. In FIG. 6, the engagement between the shield front engagement structure 991 and the shield sleeve 70 can also be seen. Furthermore, projections 922a of the retainer member 92 engage with the medicament container holder 20.

At the distal end of the medicament delivery device 1, it can be seen that the first resilient member 80, i.e. the shield spring is coaxially arranged in its loaded state on the shield driver 120 and abuts with its proximal end against the shield driver flange 122 and with its distal end against the circumferential ledge 111 of the tubular increment element 110.

Furthermore, the shield sleeve 70 abuts with its distal surface against the shield driver flange 122 of the shield driver 120.

FIG. 6 also shows the radial housing connections 22 of the medicament container holder 20 with which the medicament container holder 20 is fixedly connected to the housing 10.

Figure 7:
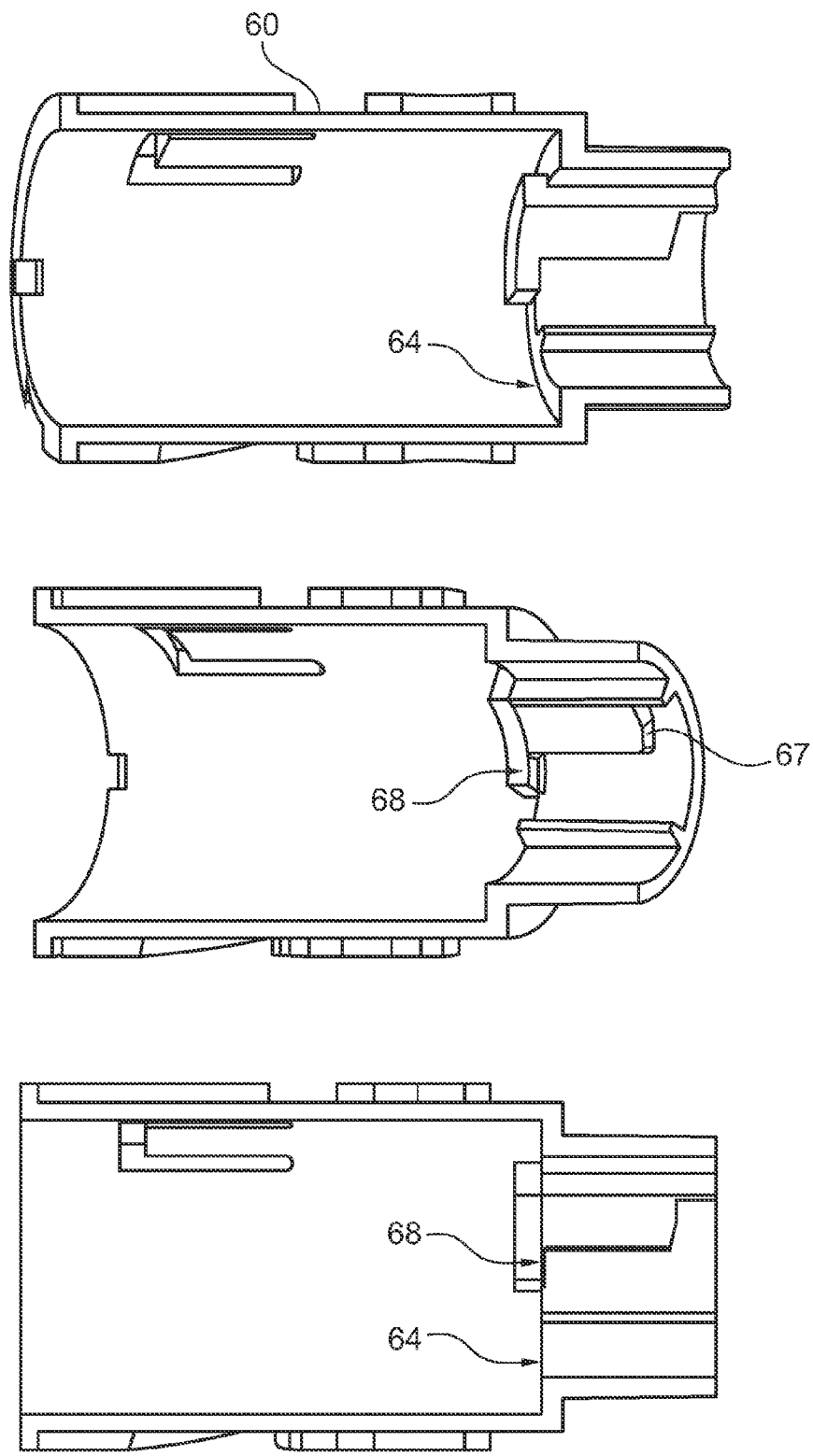
FIG. 7 shows a perspective sectional view of the plunger locking means of the medicament delivery device according to the preferred embodiment of the invention in the initial position.

FIG. 7 shows a perspective sectional view of the plunger locking means 60. In the top drawing of FIG. 7, an abutment surface 64 is shown that is formed by an inner step of the plunger locking means 60 resulting in a reduced diameter of the plunger locking means 60 at its distal end compared to the proximal part of the plunger locking means 60. The abutment surface 64 forms a distal support surface against the distal end of the housing of the medicament container holder 20.

In the middle drawing of FIG. 7, two abutment surfaces 67 and 68 are shown. The more distal abutment surface 67 forms an initial abutment surface for the plunger rod 40. In particular, a plunger rod stop rib 43 provided at the outer surface of the plunger rod 40 (see FIG. 2) abuts axially against the initial abutment surface 67 when the medicament delivery device 1 is in its initial locked state. In the intermediate priming state, the plunger rod stop rib 43 is rotationally and axially moved to the priming abutment surface 68, as will be described in more detail in the context of FIG. 8.

Finally, the lower drawing of FIG. 7 shows that the abutment surface 64 for the medicament container holder 20 and the priming abutment surface 68 are located in the same plane perpendicular to the longitudinal axis of the medicament delivery device 1.

Figure 8:
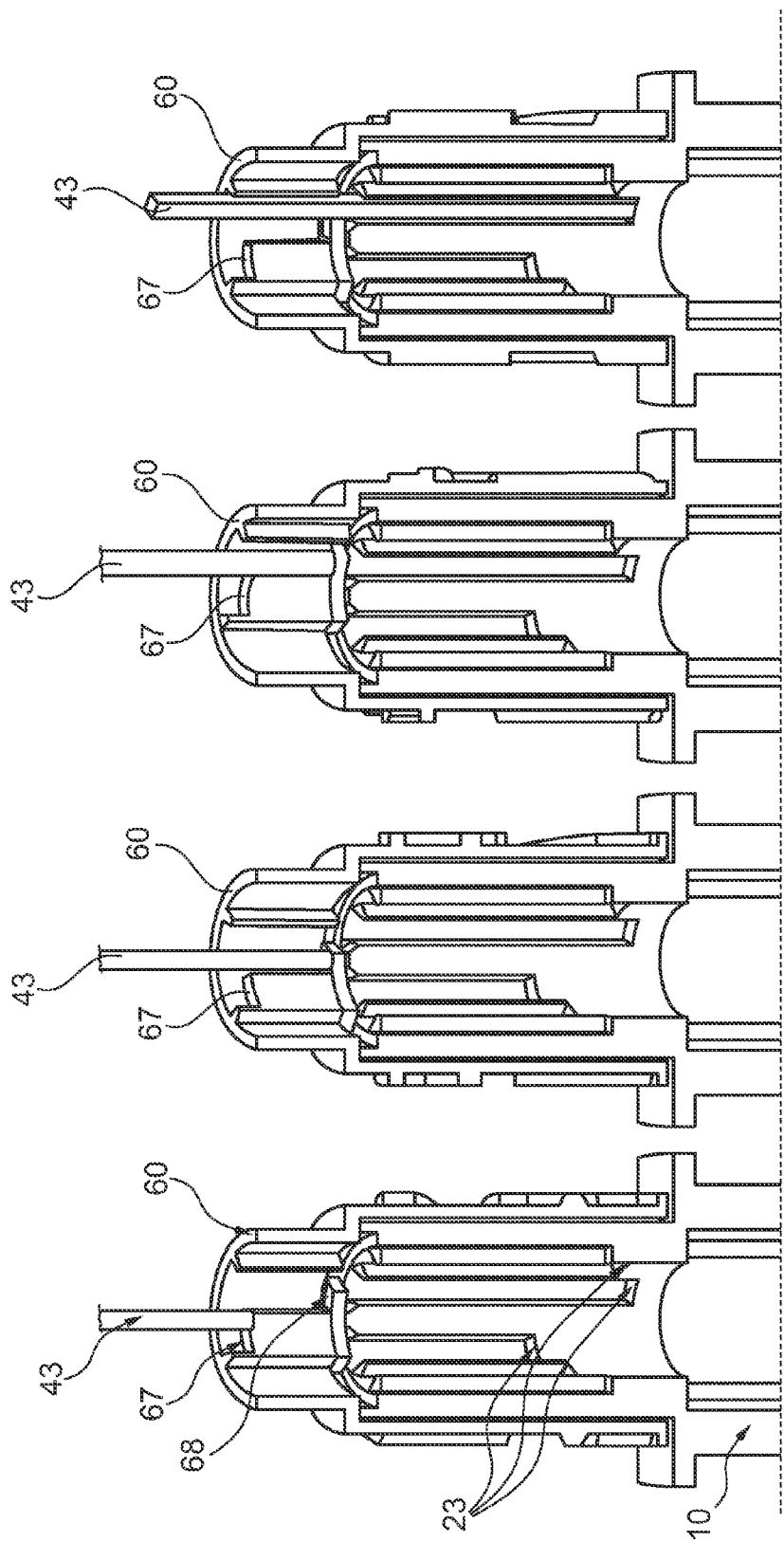
FIG. 8 shows another perspective sectional view of the plunger locking means of the medicament delivery device according to the preferred embodiment of the invention.

FIG. 8 shows a sequence of four steps visualizing the position of the plunger rod stop rib 43 relative to the plunger locking means 60, as well as the position of the plunger locking means 60 relative to the medicament container holder 20, at different states of the medicament delivery device 1.

The left-most drawing in FIG. 8 shows the initial state of the medicament delivery device 1. As mentioned above, in this state, the plunger rod stop rib 43 abuts against the initial abutment surface 67. In the priming state of the medicament delivery device 1 (second left drawing in FIG. 8), the plunger rod stop rib 43 abuts against the priming abutment surface 68. Thus, the plunger locking means 60 has been rotated relative to the plunger rod 40, and due to the force applied onto the plunger rod 40 by the second resilient member 50, the plunger rod 40 was moved axially towards the proximal end of the medicament delivery device, and then abuts against the priming abutment surface 68.

The second drawing from the right in FIG. 8 visualizes how a certain dose can be set. The medicament container holder 20 comprises in its distal part 21 one or more inner dose grooves 23 having different axial lengths. When a dose is set by a user by rotating the dose knob 103 (as will be described in more detail below), the plunger locking means 60 with the plunger rod "parked" at the priming abutment surface 68 is rotated relative to the medicament container holder 20 so that the gap that is shown right of the priming abutment surface 68 is brought into alignment with the appropriate inner dose groove.

The right drawing in FIG. 8 shows the medicament delivery state when the injection is completed. It can be seen that the plunger rod 40 with its plunger rod stop rib 43 was displaced further axially towards the proximal end of the medicament delivery device 1, and now abuts against the abutment surface formed by the inner dose groove 23. Further, since the abutment surface 64 for the medicament container holder 20 and the priming abutment surface 68 are located in the same plane perpendicular to the longitudinal axis of the medicament delivery device 1, then the distance between said plane and said abutment surface formed by the inner dose groove 23 is considered to have a dimension controlling the dose accuracy.

Figure 9:
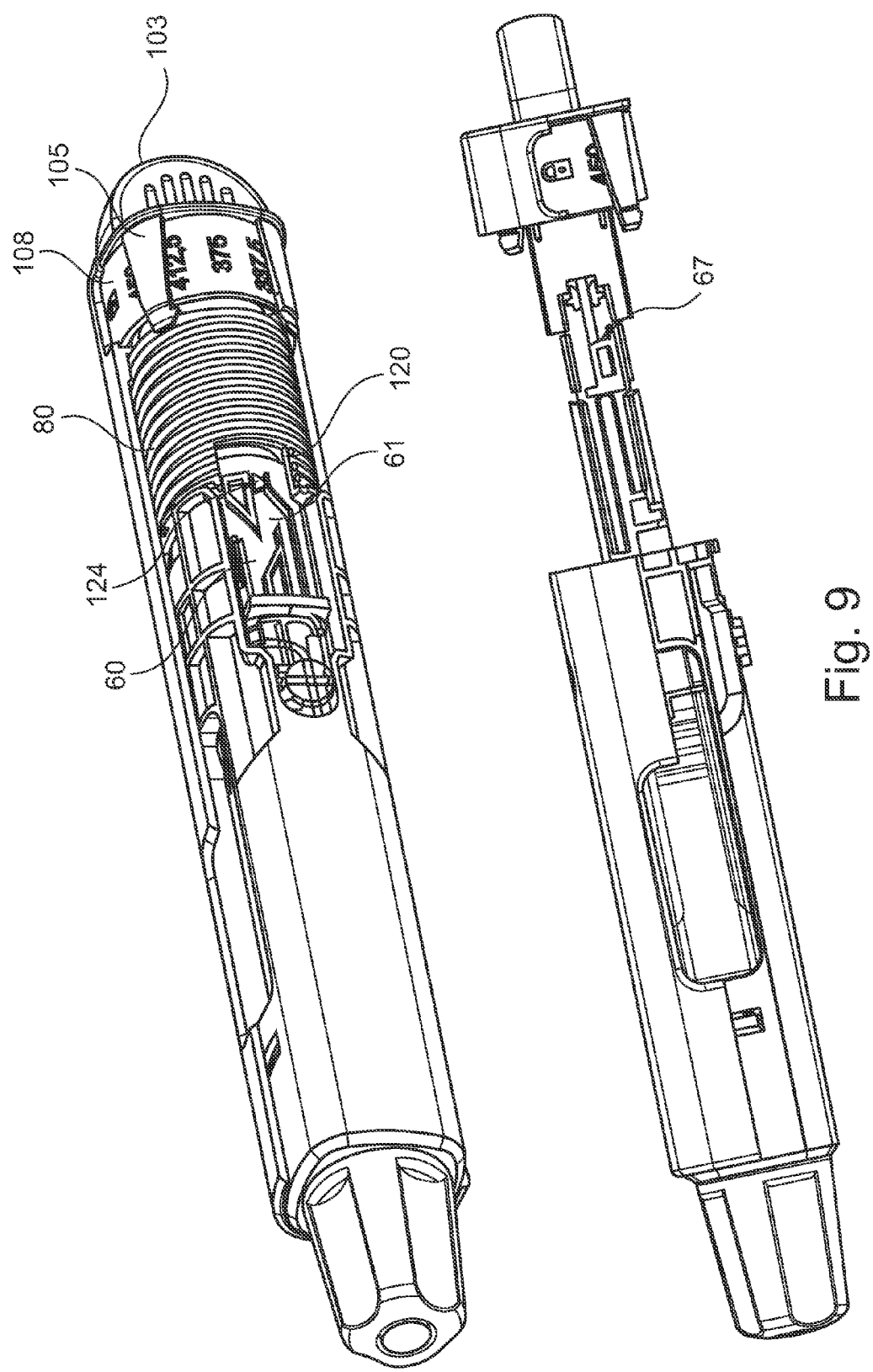
FIG. 9 shows two partially broken away perspective views of the medicament delivery device in its initial state.

FIG. 9 shows two partially broken away perspective views of the medicament delivery device 1 in its initial state. The upper drawing shows that the shield driver 120 engages with an inner guide protrusion 124 into the outer groove structure 61 of the plunger locking means 60. That is, the shield driver 120 is connected to the plunger locking means 60 by guiding means on tracks of the plunger locking means 60. Furthermore, as can be seen in the lower drawing in FIG. 9, the proximal surface of the plunger rod stop rib 43 abuts against the initial abutment surface 67 of the plunger locking means 60 (in this view, the surrounding plunger locking means 60, shield drive 120 and spring 80 are "removed").

Figure 10:
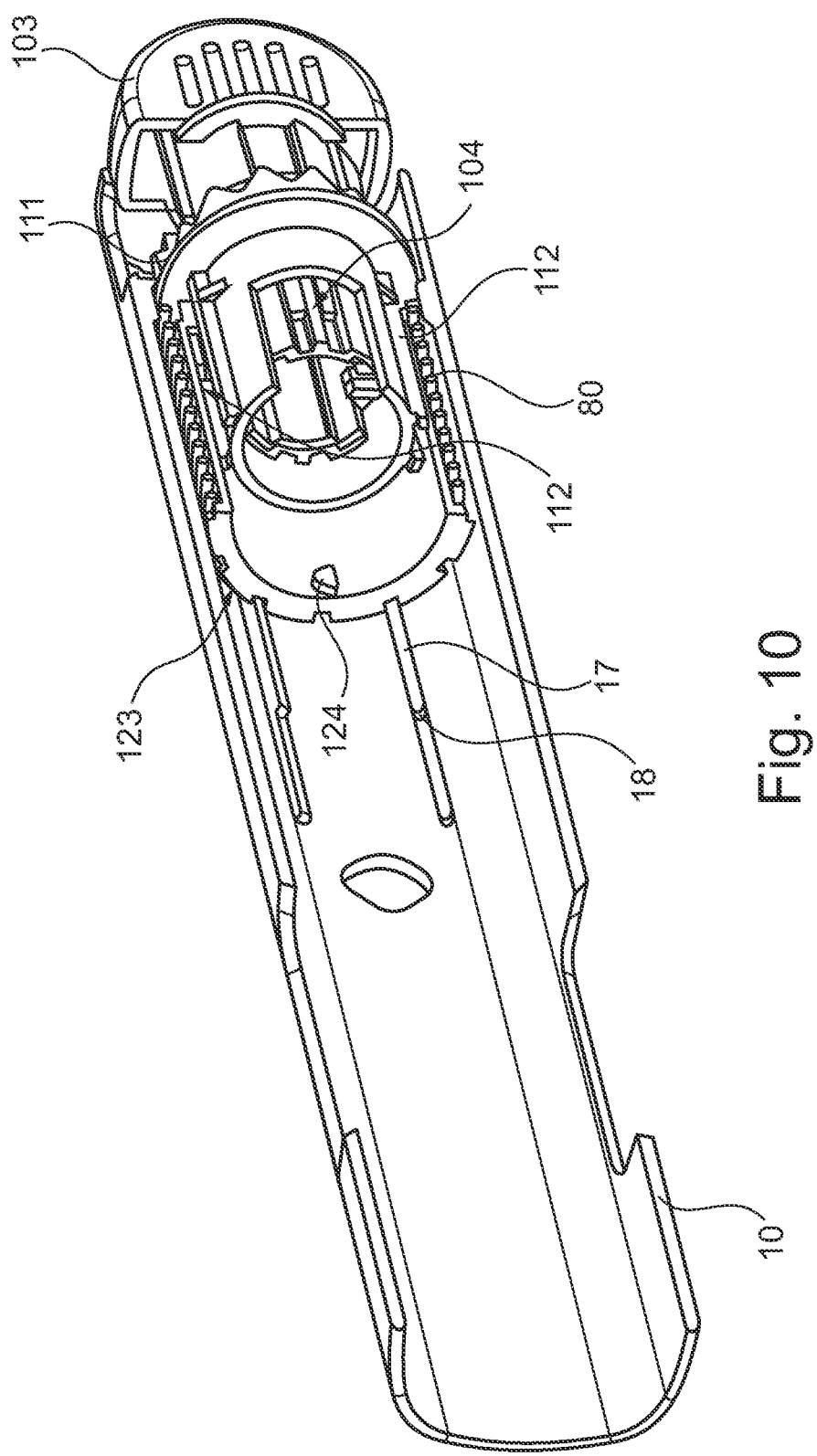
FIG. 10 shows another partially broken away perspective view of the medicament delivery device in its initial state.

The partially broken away perspective view of FIG. 10 shows how the rotational lock structure 104 of the dose member engagement part 102 engages with a mating inner lock structure of the tubular increment element 110. It furthermore can be seen that the shield link lock structure 112 at the outer surface of the tubular increment element 110 engages into a corresponding inner lock structure of the shield driver 120. Thus, the tubular increment element 110 is rotatably locked to the dose member 101 but axially slidable in relation to the dose member 101. Moreover, the shield driver 120 is rotatably locked to the tubular increment element 110 but axially slidable in relation to the tubular increment element 110.

FIG. 10 also shows that the shield driver flange 122 comprises a plurality of shield driver flange indentations 123 which receive axial ribs 17 provided on the inner surface of the housing 10 that a provide a shield link rotational lock structure. Due to this lock structure, in the initial state of the medicament delivery device 1, the shield driver 120 is rotatably locked to the housing 10 but axially slidable in relation to the housing 10. FIG. 10 also shows that the axial ribs 17, i.e. the shield link rotational lock structure, comprise a step configuration in that the height of the ribs 17 decreases a third distance proximal to the flange 122 (see step 18). Having passed the step 18 proximally, the shield driver 120 is no longer rotatably locked but can rotate relative to the housing.

Due to the locking engagement between the dose member 101 and the tubular increment element 110, between the tubular increment element 110 and the shield driver 120, and between the shield driver 120 and the housing 10, the dose knob 103 is prevented to be turned before the outer cap 91 is removed.

Figure 11:
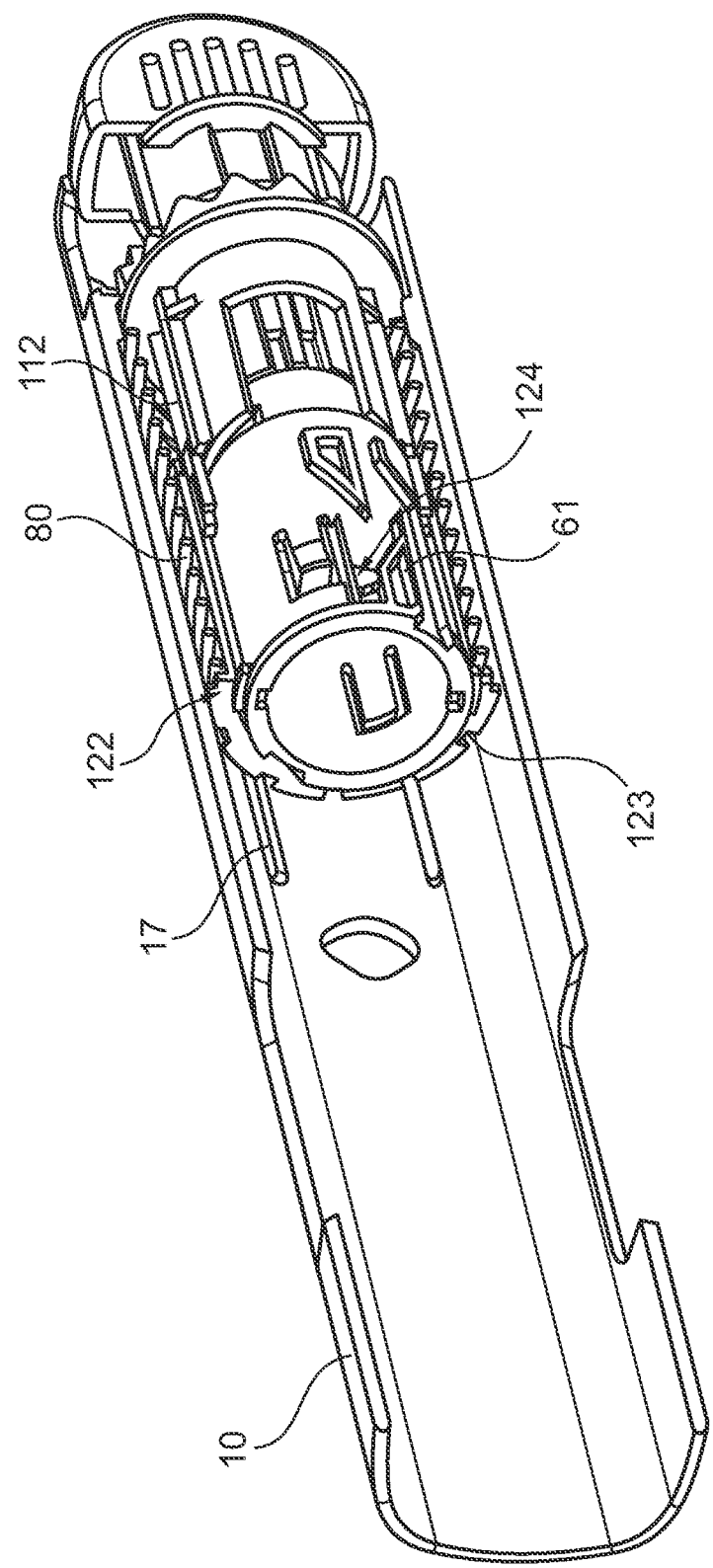
FIG. 11 shows a similar partly broken away perspective view as FIG. 10, however, in the priming state of the medicament delivery device.

FIG. 11 shows a similar partly broken away perspective view as FIG. 10. However, FIG. 11 shows the medicament delivery device 1 in the priming state. The outer cap 91 has already been removed, and the first resilient member 80 moved the shield driver 120 (and thus the shield sleeve 70) in proximal direction. The inner guide protrusion 124 thereby moved in the outer groove structure 61 of the plunger locking means 60 in proximal direction. Due to the shape of the outer groove structure 61, movement of the inner guide protrusion 124 in proximal direction results in a rotational movement of the plunger locking means 60 from its initial state to the priming state (see FIG. 8). Thus, the plunger rod stop rib 43 is now moved from the initial abutment surface 67 to the priming abutment surface 68 (not shown in FIG. 11).

Furthermore, the shield driver flange 122 with its indentations 123 has now passed beyond the step 18 in the ribs 17 of the housing 10 (see FIG. 10) so that the shield driver 120 is now released from the housing 10. Thus, the dose member 101 can now be rotated in order to set a dose.

On the other hand, due to the rotational movement of the plunger locking means 60, outwardly extending protrusions at the proximal end of the plunger locking means 60 are moved into engagement with a corresponding abutment surface at the distal end of the shield sleeve 70. This causes the shield sleeve 70 to be axially locked in its position extending from the proximal end of the housing 10. Thus, in the priming state of the medicament delivery device 1, the medicament delivery device 1 cannot be inadvertently be used. If a user were to press the medicament delivery device 1 onto a delivery site, the shield sleeve 70 would not move backwards into the housing 10. This prevents use of the medicament delivery device before an appropriate dose is set.

When the dose member 101 is rotated in order to set a dose, the dose drum 108, the tubular increment element 110, the shield driver 120, the plunger locking means 60, the plunger rod 40, the plunger rod guide rod 55, and the first and second resilient members 80, 50 are also rotated such that the plunger rod stop rib 43 of the plunger rod 40 is aligned with the selected inner dose groove 23 within the medicament container holder 20.

Due to this rotational movement of the plunger locking means 60 when setting a dose, the outward extensions of the plunger locking means 60 are moved out of engagement with the distal end of the shield sleeve 70. Thus, the shield sleeve 70 is no longer axially locked by these outwardly extending protrusions on the outer circumference of the plunger locking means 60. The medicament delivery device 1 is no ready for use.

Figure 12:
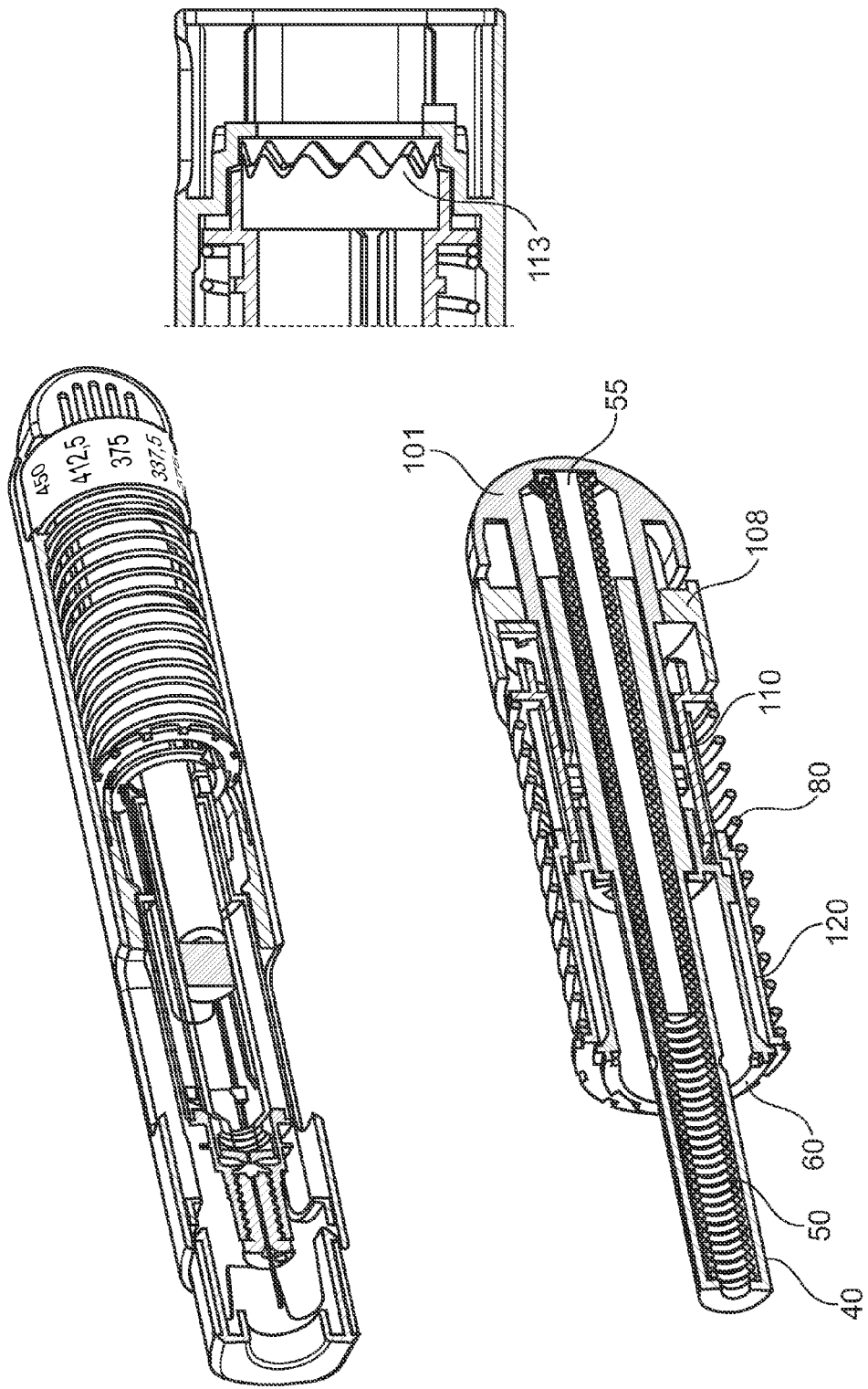
FIG. 12 shows details of the dose setting.

FIG. 12 shows in the lower drawing all elements that rotate together, as described above, when a dose is set.

The enlarged view shown in FIG. 12 shows the distal cam feature 113 of the tubular increment element 110. Upon movement of these rotating components, the tubular increment element 110 also travels axially in relation to the housing 10 due to the cam features between the tubular increment 110 and the housing 10 when a dose is dialed. Thus, step by step, the tubular increment element 110 is rotated relative to the housing 10 which results in an indication of the respective dose by dose drum 108 through window 14 of housing 10.

Figure 13:
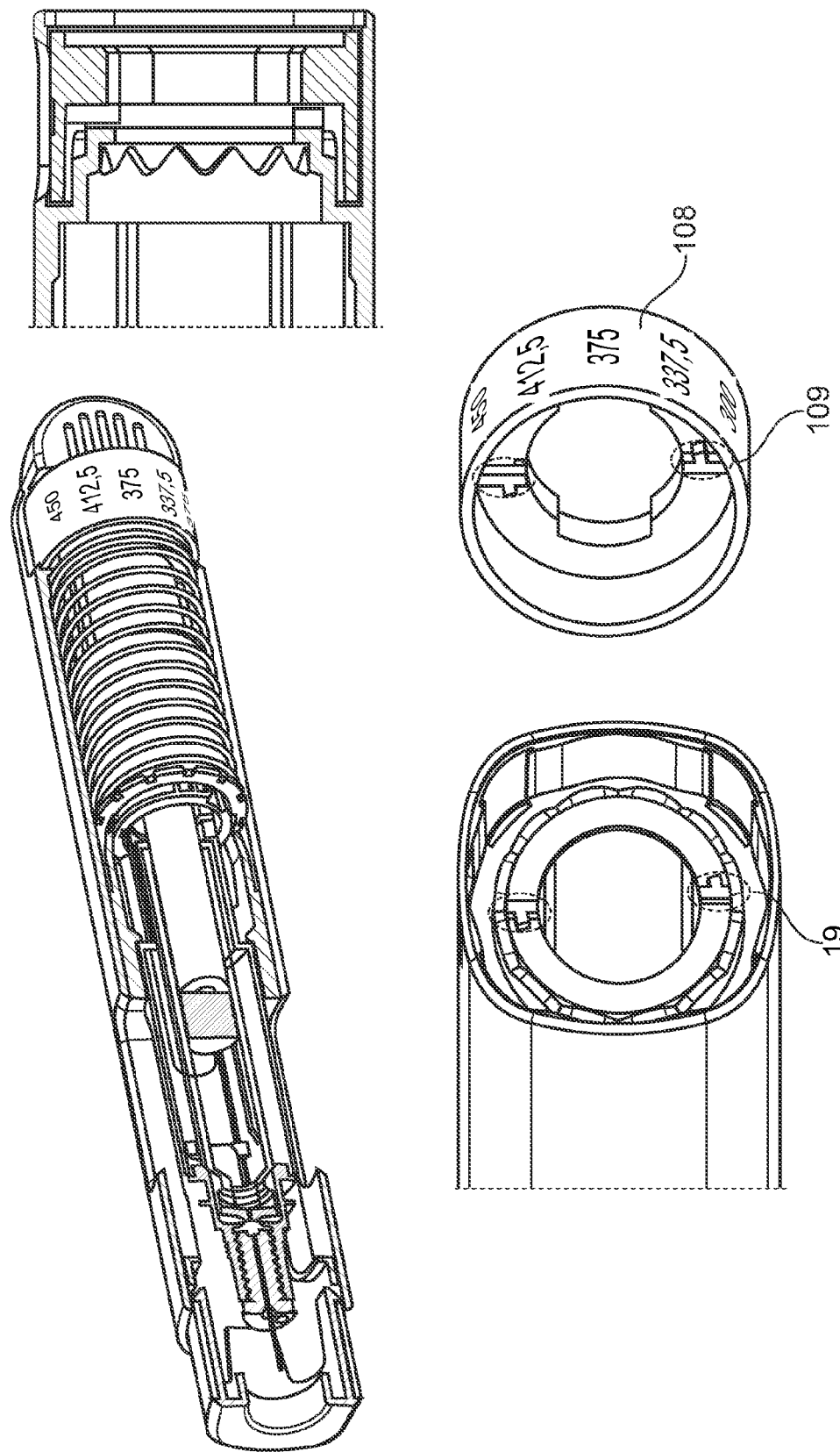
FIG. 13 shows further details of the dose setting.

This is also clear from FIG. 13. FIG. 13 shows the dose drum 108 having housing abutments 109 projecting proximally. These housing abutments 109 engage with corresponding dose drum abutments 19 projecting distally from the housing 10. This prevents the user from turning the drum knob 103 in the wrong direction, or to pass the last possible dose.

Figure 14:
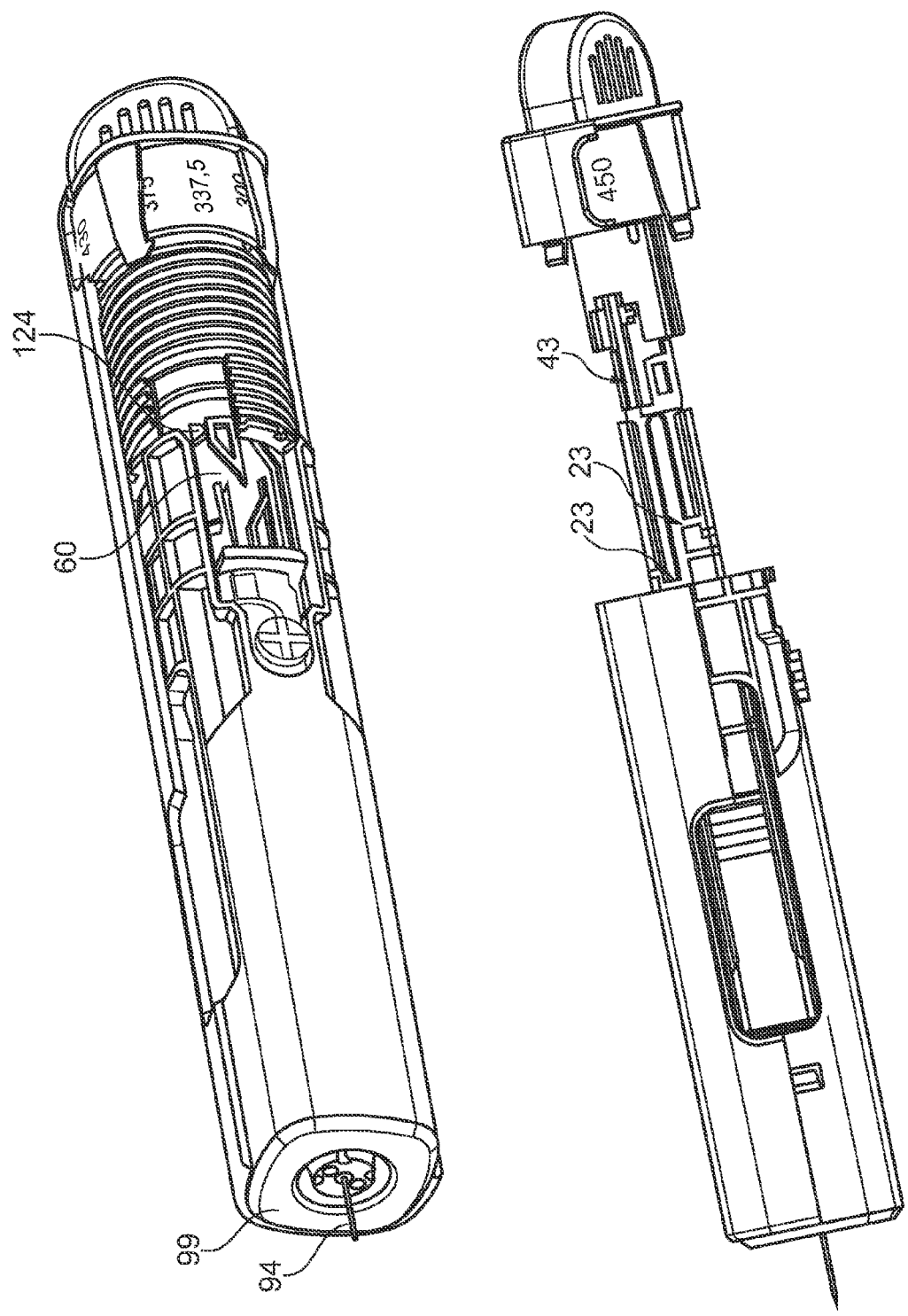
FIG. 14 shows a partially broken away perspective view of the medicament delivery device upon injection activation.

FIG. 14 shows a partially broken away perspective view of the medicament delivery device 1 upon injection activation. The shield sleeve 70 and the shield driver 120 are depressed, i.e., moved distally with respect to the housing 10. Due to this movement, the shield driver 120 forces the plunger locking means 60 to turn such that the plunger rod 40 is released from the priming abutment surface 68 and moved forwardly in proximal direction until the stop ribs 43 of the plunger rod 40 abut the selected dose stop in the selected inner groove 23. As can be seen in the upper drawing of FIG. 14, the inner guide protrusion 124 has moved (along with the shield driver 120) along an inclined groove in distal direction relative to the plunger locking means 60.

Figure 15:
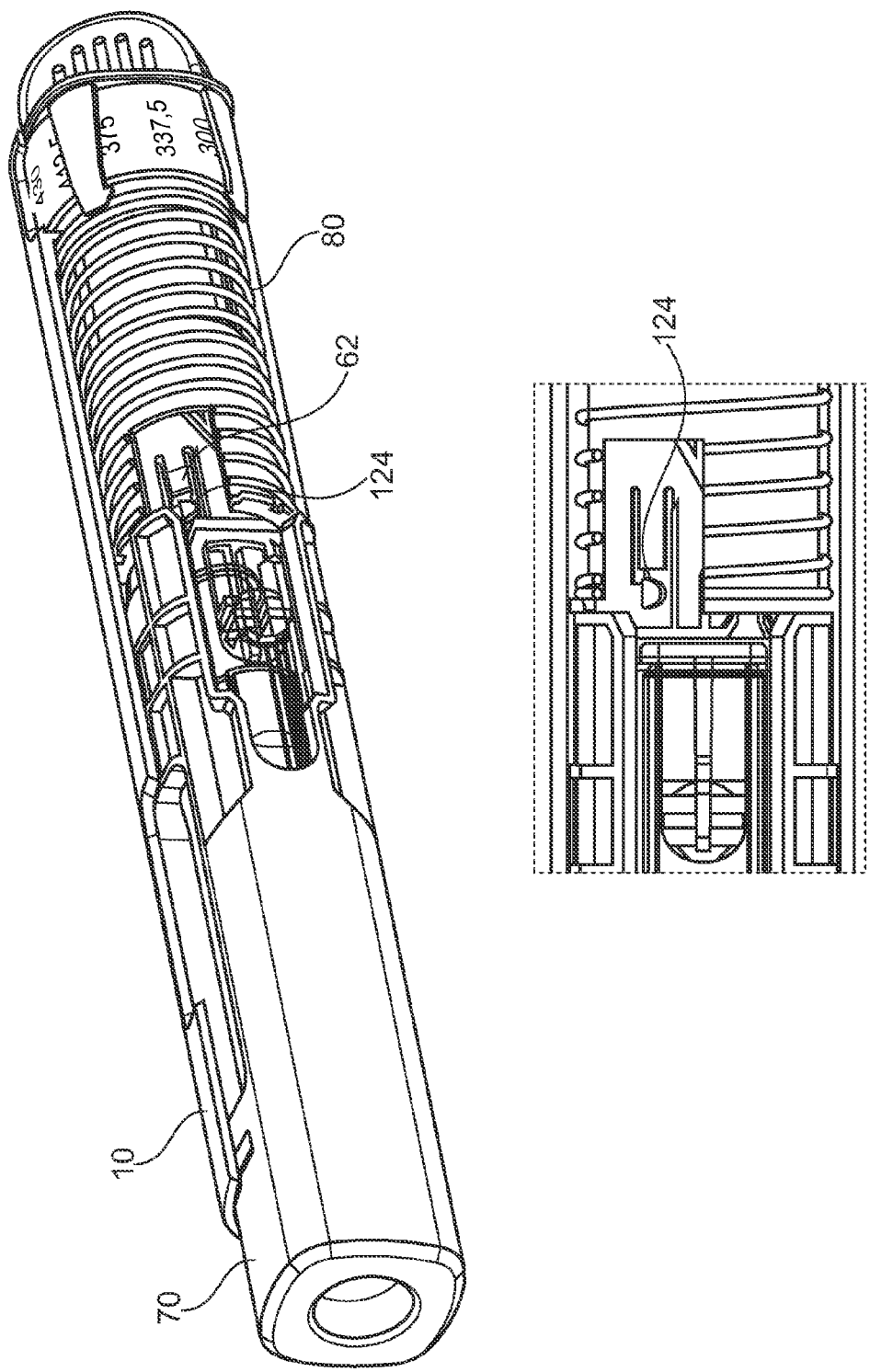
FIG. 15 shows the medicament delivery device in its locked state after injection.

FIG. 15 shows the medicament delivery device 1 in its locked state after injection. Upon removal of the medicament delivery device 1 from the delivery site, the first resilient member 80 urges the shield sleeve 70 to again protrude proximally from the housing 10. The shield driver 120 is moved proximately, and its inner guide protrusion 124 is finally locked by means of a shield link lock structure 62. Thus, after injection, the shield driver 120 and thus the shield sleeve 70 are locked by the plunger locking means 60.

Furthermore, in said state, the dose member 101 is rotatably locked in order to prevent further dose setting. In particular, the dose member 101 is rotatably locked through the tubular increment element 110, and the plunger rod 40 is rotatably locked to the medicament container holder 20.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device having an initial locked state, an intermediate priming state, and a medicament delivery state, the medicament delivery device comprising:
    a housing having a proximal end and a distal end;
    a medicament container holder arranged within the housing;
    a plunger rod arranged within the housing;
    a plunger locking device rotatable in relation to the housing and to the plunger rod and configured to hold the plunger rod in an initial locked position in the initial locked state, to release the plunger rod from the initial locked position toward a proximal end of the medicament delivery device to an intermediate priming position, to hold the plunger rod in the intermediate priming position, and to release the plunger rod from the intermediate priming position toward the proximal end of the medicament delivery device to a final delivery position;
    a shield sleeve slidably arranged at least in a proximal part of the housing;
    a first resilient member associated with the shield sleeve;
    a cap assembly at the proximal end of the housing and connected to the medicament container holder, the cap assembly comprising a removable outer cap; and
    a dose setting mechanism being locked in the initial locked state;
    wherein in the initial locked position, the cap locks the shield sleeve from axial movement toward the proximal end of the medicament delivery device to a second position; the shield sleeve, when moved into the second position by the first resilient member upon removal of the outer cap, is locked in the second position by the plunger locking device; movement of the shield sleeve to the second position results in release of the dose setting mechanism; and setting a dose with the dose setting mechanism releases locking of the shield sleeve in the second position, thereby enabling medicament delivery.

2. The medicament delivery device of claim 1, wherein movement of the shield sleeve to the second position results in rotation of the plunger locking device to release the plunger rod from the initial locked position to the intermediate priming position.

3. The medicament delivery device of claim 1, wherein the medicament container holder is configured for accommodating a medicament container having a stopper sealingly and slidably arranged inside the medicament container.

4. The medicament delivery device of claim 3, wherein the plunger rod is arranged with a proximal end thereof contactable with the stopper.

5. The medicament delivery device of claim 1, further comprising a second resilient member associated with the plunger rod.

6. The medicament delivery device of claim 1, wherein the shield sleeve and the plunger locking device are operationally connected such that axial movement of the shield sleeve toward the distal end of the medicament delivery device, when the shield sleeve is pressed against a delivery site, causes the plunger locking device to rotate.

7. The medicament delivery device of claim 6, wherein rotation of the plunger locking device results in a release of the plunger rod from the priming position.

8. The medicament delivery device of claim 7, wherein upon release of the plunger rod, the plunger rod is urged toward the proximal end of the medicament delivery device, whereby a medicament delivery is performed.

9. The medicament delivery device of claim 1, wherein the first resilient member is configured to urge further the shield sleeve toward the proximal end of the medicament delivery device when the shield sleeve is removed from a delivery site.

10. The medicament delivery device of claim 9, wherein the medicament delivery device further comprises a locking mechanism for locking the shield sleeve against moving toward the distal end of the medicament delivery device when the shield sleeve is removed from the delivery site.

11. The medicament delivery device of claim 10, wherein the locking mechanism includes the plunger locking device.

12. The medicament delivery device of claim 6, wherein operational connection between the shield sleeve and the plunger locking device includes a cam-groove mechanism.

13. The medicament delivery device of claim 5, further comprising a shield driver operationally associated with a second resilient member associated with the plunger rod such that due to an output axial force from the first resilient member, the shield sleeve is axially movable in relation to the housing a predetermined distance toward the proximal end of the medicament delivery device from the initial locked position to the second position, whereby the medicament delivery device is brought to the priming state.

14. The medicament delivery device of claim 3, wherein the cap assembly further comprises a retainer member connected to the medicament container holder.

15. The medicament delivery device of claim 14, wherein the cap assembly further comprises a hub coaxially movable within the retainer member and including a needle having a proximal end and a distal end.

16. The medicament delivery device of claim 15, wherein the cap assembly further comprises an inner cap interactively connected to the hub and the retainer member, the outer cap being coaxially arranged to the inner cap.

17. The medicament delivery device of claim 16, wherein engagement between the outer cap and the inner cap and between the inner cap and the retainer member is configured such that removal of the outer cap causes the hub to move distally such that the distal end of the needle penetrates the proximal end of the medicament container.

18. The medicament delivery device of claim 1, wherein the dose setting mechanism comprises a dose member having a dose knob projecting distally from the housing and a dose member engagement part proximal to the dose knob.

19. The medicament delivery device of claim 18, wherein the dose setting mechanism further comprises a tubular increment element coaxial to the dose member engagement part.

20. The medicament delivery device of claim 19, wherein the dose member engagement part comprises an outer rotational lock structure for rotationally locking the dose member to a mating inner lock structure of the tubular increment element.

21. The medicament delivery device of claim 19, wherein the tubular increment element comprises an outer lock structure for rotationally locking the tubular increment element to a mating inner lock structure of a shield driver operationally associated with a second resilient member associated with the plunger rod such that due to an output axial force from the first resilient member, the shield sleeve is axially movable in relation to the housing a predetermined distance toward the proximal end of the medicament delivery device from the initial locked position to the second position, whereby the medicament delivery device is brought to the priming state.

22. The medicament delivery device of claim 19, wherein the tubular increment element comprises an outer circumferential ledge forming a distal abutment surface for the second resilient member.

23. The medicament delivery device of claim 19, wherein the tubular increment element comprises a distal cam device mating with a distal cam device of the housing configured to allow distal movement of the tubular increment element during rotational movement of the tubular increment element.

* * * * *